United States Patent [19]

Hassdenteufel

[11] Patent Number: 4,574,159
[45] Date of Patent: Mar. 4, 1986

[54] PROCESS FOR THE PREPARATION OF O-METHYL-N-VINYLURETHANE

[75] Inventor: Jürgen-Rolf Hassdenteufel, Cologne, Fed. Rep. of Germany

[73] Assignee: Bayer Aktiengesellschaft, Leverkusen, Fed. Rep. of Germany

[21] Appl. No.: 614,571

[22] Filed: May 25, 1984

[30] Foreign Application Priority Data

May 28, 1983 [DE] Fed. Rep. of Germany ....... 3319451

[51] Int. Cl.$^4$ .......................................... C07C 125/065
[52] U.S. Cl. .................................................. 560/157
[58] Field of Search .......................................... 560/157

[56] References Cited

U.S. PATENT DOCUMENTS

| | | | |
|---|---|---|---|
| 2,592,254 | 4/1952 | Dickey | 560/157 |
| 3,336,368 | 8/1967 | Schwiersch | 560/157 |
| 3,336,369 | 8/1967 | Schwiersch | 560/157 |
| 3,914,304 | 10/1975 | Schnabel | 564/224 |

Primary Examiner—Michael L. Shippen
Attorney, Agent, or Firm—Sprung, Horn, Kramer & Woods

[57] ABSTRACT

After pyrolysis of N-α-methoxyethyl-O-methylurethane, it is possible to obtain very pure O-methyl-N-vinylurethane by cooling the pyrolysate and separating off the crystalline product. After separating off the O-methyl-N-vinylurethane, it is possible to react the mother liquor with methanol in the presence of bases and then to pass the reaction product to another pyrolysis.

14 Claims, No Drawings

PROCESS FOR THE PREPARATION OF O-METHYL-N-VINYLURETHANE

The invention relates to a process for the preparation of O-methyl-N-vinylurethane by pyrolysis of N-α-methoxyethyl-O-methylurethane and subsequent working-up.

It is known that O-methyl-N-vinylurethane can be prepared by adding alcohols to vinyl isocyanate (Soc. Chem. Belg. 66, 229–243 (1957)). This process cannot be carried out industrially since it starts from acryloyl chloride, which is not readily accessible industrially, and includes thermal decomposition of explosive acryloyl azide.

The preparation of O-methyl-N-vinylurethane by transvinylation of carbamic esters with alkyl vinyl ethers is also known (U.S. Pat. No. 3,019,231). Using this process the O-methyl-N-vinylurethane is obtained in only low yields. In addition, it is necessary to use a mercury salt catalyst.

O-Methyl-N-vinylurethane can also be prepared by reacting 3-vinyl-1,4,2-dioxazol-5-one with alcohols (U.S. Pat. No. 3,715,385). This process is elaborate and cannot be transferred to industry.

A process for the preparation of O-methyl-N-vinylurethane has been found, which is characterised in that N-α-methoxyethyl-O-methylurethane is pyrolysed, and the pyrolysate is cooled.

The process according to the invention can be illustrated by the reaction equation below:

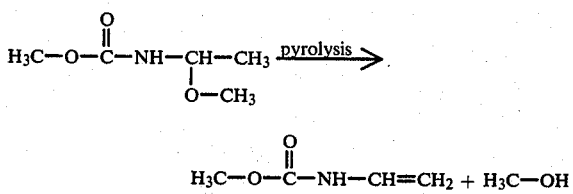

N-α-Methoxyethyl-O-methylurethane for the process according to the invention is known per se (European Pat. No. A-0,009,697). It can be prepared by electrochemical oxidation of N-ethyl-O-methylurethane.

The pyrolysis according to the invention is carried out by heating the N-α-methoxyethyl-O-methylurethane under a pressure in the range from 5 to 1,000 mbar, preferably in the range of 50–150 mbar, at a temperature in the range from 150° to 600° C., preferably from 200° to 400° C.

On pyrolysis, in addition to O-methyl-N-vinylurethane, essentially N-α-methoxyethyl-O-methylurethane (starting material), N-ethyl-O-methylurethane, O-methylurethane and methanol are also obtained.

Separation of this pyrolysis product by distillation is impossible even in vacuo since the substances are unstable to heat and readily polymerize.

According to the invention, the separation of the O-methyl-N-vinylurethane out of the pyrolysis mixture is carried out by cooling. The cooling is preferably carried out to a temperature in the range from 20° to −80° C., preferably from 10° to −40° C.

The pyrolysis product can contain between 20 and 60% by weight of methanol. Before cooling the pyrolysis product, it is preferable to separate out the methanol entirely or partially. In general, the methanol is separated out until the residual amount is less than or equal to 5%, preferably less than or equal to 2%, based on the pyrolysis product.

The separation out of the methanol is carried out in a mild manner by distilling out the methanol under pressures below 500 mbar, preferably in the pressure range below or at 200 mbar.

It is also possible to remove the methanol using a film evaporator.

In the cooling of the pyrolysis mixture according to the invention, O-methyl-N-vinylurethane crystallizes out in a very pure form. The purity is generally greater than 97%, and, preferably, almost pure product is obtained.

As a rule, 1 to 6 hours are required for the crystallizing out of the O-methyl-N-vinylurethane.

The O-methyl-N-vinylurethane which has crystallised out can be separated out in a manner known per se, for example by centrifugation.

The mother liquor obtained after separating out the O-methyl-N-vinylurethane still contains, inter alia, N-α-methoxyethyl-O-methylurethane as the starting material and O-methyl-N-vinylurethane which has not been separated out. In one embodiment of the process according to the invention, this mother liquor is returned to a new pyrolysis.

In a particularly preferred embodiment of the process according to the invention, methanol is added, in the presence of bases, onto the O-methyl-N-vinylurethane in the mother liquor and thus a mixture which has been enriched in N-α-methoxyethyl-O-methylurethane is obtained, and this can be returned to a new pyrolysis.

The addition of methanol onto the O-methyl-N-vinylurethane takes place selectively and does not alter the remaining compounds in the mother liquor.

The amount of methanol for the addition depends on the amount of O-methyl-N-vinylurethane in the mother liquor. In general, equimolar amounts, or a 1- to 5-fold excess of the alcohol, are used.

Possible bases for the addition of the methanol onto O-methyl-N-vinylurethane are alcoholates, basic ion exchangers and tertiary amines.

Alcoholates are essentially the alkali metal alcoholates, preferably the sodium and potassium alcoholates of lower alcohols ($C_1$–$C_6$), preferably alkali metal methylate, ethylate and butylate. Sodium methylate is particularly preferred.

Basic ion exchangers are essentially strongly basic anion exchangers based on crosslinked quaternized polyvinylbenzylamine which, for use, is in the form of the free base. The ion exchanger can be either in the form of a gel or macroporous.

Tertiary amines for the process according to the invention are compounds of the formula

in which
$R^1$, $R^2$ and $R^3$ are identical or different and represent a lower alkyl radical.

In this context, lower alkyl generally denotes a straight-chain or branched hydrocarbon radical having 1 to, say, 6 carbon atoms. Preferred tertiary amines are triethylamine, tripropylamine and tributylamine.

The amount of the base for the addition of methanol depends on the amount of O-methyl-N-vinylurethane in the mother liquor. In general, 1 to 10 mole-%, preferably 2 to 8 mole-%, of the base, based on the O-methyl-N-vinylurethane to be reacted, are employed.

In general, the temperature for the addition of methanol is in the range from 0° to 80° C., preferably from 20° to 60° C.

The amount of O-methyl-N-vinylurethane in the mother liquor can readily be determined by gas chromatography.

The process according to the invention can be carried out both discontinuously and continuously. In the continuous procedure, the mother liquor which has been enriched in N-α-methoxyethyl-O-methylurethane by the addition of methanol is returned to the pyrolysis.

The process according to the invention in the preferred embodiment can be carried out, for example, as follows:

For the pyrolysis, the N-α-methoxyethyl-O-methylurethane is preferably vaporized under a subatmospheric pressure and passed in the form of a gas through a tube reactor heated to the pyrolysis temperature. Thereafter, where appropriate, the methanol is largely separated out, and the pyrolysate is cooled for some time to crystallize out the O-methyl-N-vinylurethane.

The O-methyl-N-vinylurethane which has crystallized out is advantageously removed by centrifugation.

The mother liquor can be returned to a pyrolysis. However, it is advantageous to add on methanol in the presence of a base and to pass the mixture which has been enriched in N-α-methoxyethyl-O-methylurethane to another pyrolysis.

The process according to the invention makes it possible to prepare O-methyl-N-vinylurethane on an industrial scale. O-Methyl-N-vinylurethane is obtained in high purity and high yields.

It is surprising that a very pure product is obtained in the separation out according to the invention of the O-methyl-N-vinylurethane, because all other customary processes for separating out, for example distillation, are unsatisfactory.

It is also surprising that the methanol can be selectively added onto the O-methyl-N-vinylurethane, and other undesired by-products are avoided.

The O-methyl-N-vinylurethane prepared by the process according to the invention can be used for the preparation of homopolymers and copolymers and their secondary products, such as, for example, basic ion exchangers.

EXAMPLE 1

(a) Pyrolysis 997.5 g (7.5 mol) of N-α-methoxyethyl-O-methylurethane are passed, over a period of 10 hours, through a tube reactor under a vacuum of 100 mbar and at temperatures between 200° and 400° C., and the emerging pyrolysis gases are condensed to form a pyrolysate. The pyrolysate contains 727.2 g (7.2 mol) of O-methyl-N-vinylurethane which corresponds to a yield of 96% of theory.

(b) Separation Out of the Methanol

The methanol contained in the pyrolysate obtained from the pyrolysis is almost completely removed using a film evaporator under a pressure of 75 mbar, at a temperature of 45° C. and a throughput of about 100 g/h. 773.6 g of concentrated pyrolysate, which contains about 1.8% of methanol, are obtained.

(c) Cooling the Pyrolysate

The pyrolysate is cooled to −15° C. in a thermostat for 3 h. During this, the O-methyl-N-vinylurethane crystallizes out and can be straightforwardly separated out by centrifugation.

(d) Separation Out of the O-methyl-N-vinylurethane

The cooled and concentrated pyrolysate is centrifuged at about 3,000 rpm for 6 minutes. After completion of centrifugation, 695.0 g of pure O-methyl-N-vinylurethane (purity 99.9%) and 78.6 g of mother liquor, the composition of which is detailed in the table below, are obtained:

| Sample | Weight [g] | Data in % or g | Composition | | | | |
| --- | --- | --- | --- | --- | --- | --- | --- |
| | | | MeOH | EU | MU | VU | U |
| concentrated crude pyrolysate employed | 773.6 | %<br>g | 1.8<br>13.9 | 0.3<br>2.3 | 3.2<br>24.8 | 93.5<br>723.3 | 1.2<br>9.3 |
| vinyl product obtained 89.8% by weight | 695.0 | %<br>g | 0.0<br>0.0 | 0.0<br>0.0 | 0.1<br>0.7 | 99.9<br>694.3 | 0.0<br>0.0 |
| mother liquor obtained 10.2% by weight | 78.6 | %<br>g | 17.7<br>13.9 | 2.9<br>2.3 | 30.7<br>24.1 | 36.9<br>29.0 | 11.8<br>9.3 |

MeOH = methanol
EU = N—ethyl-O—methylurethane
MU = N—α-methoxyethyl-O—methylurethane
VU = O—methyl-N—vinylurethane
U = O—methylurethane

(e) Addition of Methanol Onto the O-methyl-N-vinylurethane Contained in the Mother Liquor 78.6 g of the mother liquor and 19.0 g (0.59 mol) of methanol (about 4-fold molar excess based on the O-methyl-N-vinylurethane in the mother liquor) are initially introduced into a multineck reaction flask equipped with a stirrer, condenser and dropping funnel, 0.62 g (0.0115 mol) of sodium methylate in 5 ml of methanol are added, and the mixture is stirred at room temperature. The addition of methanol, the progress of which can be followed by removing samples which are analyzed by gas chromatography, is complete after about 3 hours.

The mother liquor which has been enriched in N-α-methoxyethyl-O-methylurethane has the following composition:

| Sample | Weight* [g] | Data in % or g | Composition | | | | |
| --- | --- | --- | --- | --- | --- | --- | --- |
| | | | MeOH | EU | MU | VU | U |
| Mother liquor + MeOH before addition | 101.6 | %<br>g | 36.3<br>36.9 | 2.3<br>2.3 | 23.7<br>24.1 | 28.5<br>29.0 | 9.2<br>9.3 |
| Mother liquor after addition | 101.6 | %<br>g | 27.4<br>27.8 | 2.3<br>2.3 | 61.0<br>62.0 | 0.2<br>0.2 | 9.1<br>9.3 |

*not taking the catalyst into account (f) Recycling of the Enriched Mother Liquor The enriched mother liquor is returned to the pyrolysis. In the process described in Section (e), a conversion of 99.3% and a selectivity of 100% are obtained.

EXAMPLE 2

A pyrolysate having a very low content of O-methyl-N-vinylurethane is employed in the example.

(a) Separation Out of O-methyl-N-vinylurethane 600.0 g of cooled and concentrated pyrolysate is centrifuged at about 3,000 rpm for 7 minutes. After completion of centrifugation, 474.4 g of pure O-methyl-N-vinylurethane (purity 99.7%) and 125.5 g of mother liquor, the composition of which is detailed in the table below, are obtained:

| Sample | Weight [g] | Data in % or g | MeOH | EU | MU | VU | U |
|---|---|---|---|---|---|---|---|
| concentrated crude pyrolysate employed | 600.0 | % | 3.3 | 0.6 | 10.8 | 83.8 | 1.5 |
|  |  | g | 19.8 | 3.6 | 64.8 | 502.8 | 9.0 |
| vinyl product obtained 79.1% by weight | 474.4 | % | 0.0 | 0.0 | 0.3 | 99.7 | 0.0 |
|  |  | g | 0.0 | 0.0 | 1.4 | 473.0 | 0.0 |
| mother liquor obtained 20.9% by weight | 125.5 | % | 15.8 | 2.9 | 50.4 | 23.7 | 7.2 |
|  |  | g | 19.8 | 3.6 | 63.3 | 29.8 | 9.0 |

MeOH = methanol
EU = N—ethyl-O—methylurethane
MU = N—α-methoxyethyl-O—methylurethane
VU = O—methyl-N—vinylurethane
U = O—methylurethane (b) Addition of Methanol Onto the O-methyl-N-vinylurethane Contained in the Mother Liquor 125.5 of the mother liquor and 9.2 g (∼0.29 mol) of methanol (about 3-fold molar excess based on the O-methyl-N-vinylurethane in the mother liquor) are initially introduced into a multineck reaction flask equipped with a stirrer, condenser and dropping funnel, and 0.9 g (0.009 mol) of triethylamine in 1 ml of methanol are added. The mixture is heated, with stirring, to 50° C. The addition of methanol, the progress of which can be followed by removing samples which are analysed by gas chromatography, is complete after about 6 hours.

The mother liquor enriched in N-α-methoxyethyl-O-methylurethane has the following composition:

| Sample | Weight* [g] | Data in % or g | MeOH | EU | MU | VU | U |
|---|---|---|---|---|---|---|---|
| Mother liquor + MeOH before addition | 135.5 | % | 22.0 | 2.7 | 46.7 | 22.0 | 6.6 |
|  |  | g | 29.8 | 3.7 | 63.3 | 29.8 | 8.9 |
| Mother liquor after addition | 135.5 | % | 15.1 | 2.7 | 75.3 | 0.3 | 6.6 |
|  |  | g | 20.5 | 3.7 | 102.0 | 0.4 | 8.9 |

*not taking the catalyst into account (c) Recycling the Enriched Mother Liquor

The enriched mother liquor is returned to the pyrolysis. In the process described in Section (e), a conversion of 98.7% and a selectivity of 100% are obtained.

What is claimed is:

1. A process for the preparation of O-methyl-N-vinylurethane which comprises subjecting a composition consisting essentially of N-alpha-methoxyethyl-O-methylurethane to pyrolysis in a tube reactor and cooling the resultant pyrolysate, wherein substantially pure O-methyl-N-vinylurethane is separated out from said pyrolysate and the resultant mother liquor is passed to a new pyrolysis and wherein methanol is added on to the resultant mother liquor in the presence of a base.

2. A process according to claim 1, wherein said base is an alcoholate, a basic ion exchanger or a teritary amine.

3. A process according to claim 2, wherein said base is a teritary amine of the formula

wherein
$R^1$, $R^2$ and $R^3$ are identical or different and represent a lower alkyl radical.

4. A process according to claim 1, wherein said mother liquor is reacted with methanol at a temperature in the range from 0° to 80° C.

5. A process according to claim 1, wherein said base is present in an amount of 1 to 10 mol percent, based on the O-methyl-N-vinylurethane to be reacted.

6. A process according to claim 5, wherein said methanol is employed in an amount corresponding to an equimolar amount up to a 5 fold excess.

7. A process according to claim 1, wherein said N-alpha-methoxyethyl-O-methylurethane is pyrolyzed, the resulting methanol is distilled out, the concentrated pyrolysate is cooled, the temperature in the range from 20° to −80° C., the O-methyl-N-vinylurethane which crystallizes is separated out employing centrifugation, methanol is added to the resultant mother liquor in the presence of a base and the N-alpha-methoxyethyl-O-methylurethane which forms as a result thereof is subjected to pyrolysis.

8. A process for the preparation of O-methyl-N-vinylurethane which comprises subjecting N-alpha-methoxyethyl-O-methylurethane to pyrolysis, cooling the resultant pyrolysate, separating out substantially pure O-methyl-N-vinylurethane from said pyrolysate, adding methanol to the resultant mother liquor in the presence of a base and passing said resultant mother liquor to a new pyrolysis.

9. A process according to claim 8, wherein said base is an alcoholate, a basic ion exchanger or a tertiary amine.

10. A process according to claim 9, wherein said base is a tertiary amine of the formula

wherein

R$^1$, R$^2$ and R$^3$ are identical or different and represent a lower alkyl radical.

11. A process according to claim 8, wherein said mother liquor is reacted with methanol at a temperature in the range from 0° to 80° C.

12. A process according to claim 8, wherein said base is present in an amount of 1 to 10 mol percent, based on the O-methyl-N-vinylurethane to be reacted.

13. A process according to claim 12, wherein said methanol is employed in an amount corresponding to an equimolar amount up to a 5 fold excess.

14. A process for the preparation of O-methyl-N-vinylurethane which comprises subjecting N-alpha-methoxyethyl-O-methylurethane to pyrolysis, distilling out the resulting methanol, cooling the concentrated pyrolysate at a temperature in the range from 20° to −80° C., separating out the O-methyl-N-vinylurethane which crystallizes employing centrifugation, adding methanol to the resultant mother liquor in the presence of a base and subjecting the N-alphamethoxyethyl-O-methylurethane which forms as a result thereof to pyrolysis.

* * * * *